United States Patent [19]

Kawase et al.

[11] Patent Number: 4,591,498
[45] Date of Patent: May 27, 1986

[54] SHAMPOO COMPOSITION

[75] Inventors: Jiro Kawase; Takao Tokano, both of Funabashi, Japan

[73] Assignee: KAO Corporation, Tokyo, Japan

[21] Appl. No.: 661,783

[22] Filed: Oct. 17, 1984

[30] Foreign Application Priority Data

Oct. 18, 1983 [JP] Japan .................. 58-194954

[51] Int. Cl.$^4$ .......... C11D 1/18; C11D 1/38; C11D 1/50; A61K 7/06
[52] U.S. Cl. ................. 424/70; 252/541; 252/546; 252/527; 252/DIG. 13
[58] Field of Search .......... 252/DIG. 1, DIG. 13, 252/541, 546, 153, 173, 527, 174.21, DIG. 14; 424/70

[56] References Cited

U.S. PATENT DOCUMENTS

| | | | |
|---|---|---|---|
| 4,061,602 | 12/1977 | Oberstar et al. | 252/547 |
| 4,166,845 | 9/1979 | Hansen et al. | 424/78 |
| 4,220,167 | 9/1980 | Newell | 424/70 |
| 4,220,168 | 9/1980 | Newell | 424/70 |
| 4,240,450 | 12/1980 | Grollier et al. | 424/70 |
| 4,265,782 | 5/1981 | Armstrong et al. | 424/70 |
| 4,372,869 | 2/1983 | Lindemann et al. | 252/174.16 |
| 4,374,125 | 2/1983 | Newell | 424/70 |

Primary Examiner—Paul Lieberman
Assistant Examiner—John F. McNally
Attorney, Agent, or Firm—Oblon, Fisher, Spivak, McClelland & Maier

[57] ABSTRACT

In a shampoo composition which comprises an anionic surface active agent and/or an amphoteric surface active agent as a base, the following two ingredients (A) and (B) are further comprised:

(A) 0.5 to 10 wt % of an N-acyl-N-methyl-beta-alanine or its salt represented by the formula (I)

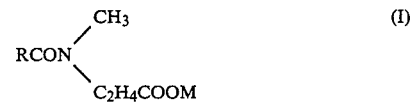

in which R represents a linear or branched, saturated or unsaturated hydrocarbon group having from 7 to 21 carbon atoms, and M represents hydrogen, alkali metal etc., (B) 0.5 to 20 wt % of one or more of ethylene oxide-added type nonionic surface active agents selected from the group consisting of polyoxyethylene alkyl or alkenyl ethers, polyoxyethylene alkylphenyl ethers, etc.

The composition has excellent detergent performance on the oily dirt exhibiting good foamability at the time of shampooing.

9 Claims, No Drawings

SHAMPOO COMPOSITION

BACKGROUND OF THE INVENTION (i) Field of the Invention

This invention relates to novel shampoo compositions and more particularly, to shampoo compositions which have high detergent action on oily dirt and exhibit good foamability at the time of shampooing.

(ii) Description of the Prior Art

Known shampoo compositions have usually utilized, as a base, anionic surface active agents such as alkylsulfates, polyoxyethylene alkylsulfates and the like, or amphoteric surface active agents such as alkylbetaines, alkylamine oxides and the like either singly or in combination thereof. However, shampoo compositions using these types of materials do not have satisfactory detergency against oily soil such as of triglycerides which may impart objectionable oiliness to hair or skin. As a consequence, there are produced some troubles such as stickiness of hair or skin, a hard-to-groom problem of hair and the like due to "greasiness", especially, inherent to the younger generation. Thus, there is a high demand for shampoo compositions with improved detergency.

On the other hand, it is known that for washing of wool, ethylene oxide added type nonionic surface active agents have higher detergency against oils and fats including triglycerides than the anionic surface active agents. Known shampoo compositions to which ethylene oxide added type nonionic surface active agents are incorporated have high detergency against oily soil. However, foamability which is one of important properties of shampoo is substantially lost. This loss becomes considerable especially under highly oil-soiling conditions. Accordingly, ethylene oxide added type nonionic surface active agents are used only for hair condition controlling purposes so as to impart smoothness to hair.

SUMMARY OF THE INVENTION

Under these circumstances, the present inventors made intensive studies to overcome the above drawback and found that incorporation of a specific type of ethylene oxide-added type nonionic surface active agent and N-acyl-N-methyl-beta-alanine or its salt to known shampoo compositions comprising, as a base, anionic surface active agents, excluding the N-acyl-N-methyl-beta-alaine and its salts in the present specification, or amphoteric surface active agents or mixtures thereof results in shampoo compositions which have high detergency against oily soil and exhibit good foamability. The present invention has been accomplished on the basis of the above finding.

Accordingly, one object of the invention is to provide a shampoo composition which comprises, in addition to an anionic surface active agent and/or an amphoteric surface active agent as a base, the following two ingredients (A) and (B), (A) 0.5 to 10 wt % of an N-acyl-N-methyl-beta-alanine or its salt represented by the formula (I)

in which R represents a linear or branched, saturated or unsaturated hydrocarbon group having from 7 to 21 carbon atoms, and M represents hydrogen, an alkali metal, ammonium, alkyl-substituted ammonium with an alkyl moiety having from 1 to 3 carbon atoms, alkanolamine having a hydroxyalkyl group having from 1 to 3 carbon atoms, and basic amino acid, and (B) 0.5 to 20 wt % of one or more of ethylene oxide-added type nonionic surface active agents selected from the group consisting of polyoxyethylene alkyl or alkenyl ethers, polyoxyethylene alkylphenyl ethers, polyoxyethylene fatty acid esters, and polyoxyethylene hardened castor oils.

DETAILED DESCRIPTION OF THE INVENTION AND PREFERRED EMBODIMENTS

Preferable examples of ingredient (A) used in the present invention include N-acyl-N-methyl-beta-alanine or its salts represented by the formula (I) in which RCO— represents an acyl group such as lauroyl, myristoyl, palmitoyl, stearoyl, oleoyl, isostearoyl or the like. M in the formula (I) includes alkali metals, ammonium, alkyl-substituted ammonium with an alkyl moiety having from 1 to 3 carbon atoms, alkanolamines having a hydroxyalkyl group having from 1 to 3 carbon atoms, or basic amino acids such as lysine, arginine and the like. Of these compounds, N-lauroyl-N-methyl-beta-alanine, or sodium and triethanolamine salts thereof are preferred. The (A) ingredient is used in the range of from 0.5 to 10 wt % (hereinafter referred to simply as %), preferably from 1 to 6%, of the total composition.

Preferable examples of (B) ingredient are mentioned below.

(1) Polyoxyethylene alkyl or alkenyl ethers which have an alkyl or alkenyl group containing from 8 to 20 carbon atoms on average and which are added 3 to 20 moles of ethylene oxide.

(2) Polyoxyethylene alkylphenyl ethers which have an alkyl group containing from 8 to 12 carbon atoms on average and which are added 3 to 20 moles of ethylene oxide.

(3) Polyoxyethylene fatty acid esters which have an alkyl or alkenyl group containing from 8 to 20 carbon atoms on average and which are added 8 to 100 moles of ethylene oxide.

(4) Polyoxyethylene hardened castor oil which are added 3 to 200 moles of ethylene oxide on average.

Of these ethylene oxide-added type nonionic surface active agents, polyoxyethylene alkyl or alkenyl ethers and polyoxyethylene hardened castor oils are preferred. These (B) ingredients are used in amounts ranging from 0.5 to 20%, preferably 0.5 to 10% and most preferably from 1 to 10%, of the total composition.

The anionic surface active agents and amphoteric surface active agents used as a base of the shampoo composition according to the present invention are as follows.

(1) Anionic Surface Active Agents (1) Linear or branched alkylbenzenesulfonates having an alkyl group containing from 10 to 16 carbon atoms on average.

(2) Alkyl or alkenyl ethersulfates which have a linear or branched alkyl or alkenyl group containing from 8 to 20 carbon atoms on average and which are added from 0.5 to 8 moles of ethylene oxide on average in one molecule.

(3) Alkyl- or alkenylsulfates having an alkyl or alkenyl group containing from 10 to 20 carbon atoms on average.

(4) Olefin sulfonates having from 10 to 20 carbon atoms on average in one molecule.

(5) Alkanesulfonates having from 10 to 20 carbon atoms on average in one molecule.

(6) Saturated or unsaturated fatty acid salts having from 10 to 20 carbon atoms on average in one molecule.

(7) Alkyl- or alkenyl ethoxy carboxylates which have an alkyl or alkenyl group containing from 10 to 20 carbon atoms on average and which are added 0.5 to 8 moles of ethylene oxide in one molecule.

(8) alpha-sulfo fatty acids or their esters represented by the following formula

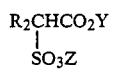

in which Y represents an alkyl group having from 1 to 3 carbon atoms or a counter ion of the anionic surface active agent, Z represents a counter ion of the anionic surface active agent, and $R_2$ represents an alkyl or alkenyl group having from 10 to 20 carbon atoms.

(9) Succinic acid derivatives of the following formula

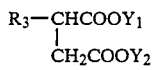

in which $R_3$ represents an alkyl or alkenyl group having from 6 to 20 carbon atoms, and $Y_1$ and $Y_2$ independently represent a counter ion.

Examples of the counter ion of these anionic surface active agents include alkali metal ions such as sodium, potassium and the like, alkaline earth metal ions such as calcium, magnesium and the like, ammonium ion, alkanolamines having from 1 to 3 alkanol groups containing 2 or 3 carbon atoms, e.g. monoethanolamine, diethanolamine, triethanolamine, triisopropanolamine and the like, and basic amino acids such as lysine, alginine and the like. Preferably, sodium, ammonium and triethanolamine are used as the counter ion.

(2) Amphoteric Surface Active Agents (1) Alkylamine oxides represented by the following formula

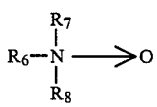

in which $R_6$ represents an alkyl or alkenyl group having from 10 to 20 carbon atoms, and $R_7$ and $R_8$ may be the same or different and are an alkyl group having from 1 to 3 carbon atoms.

(2) Alkylbetaines or sulfobetaines represented by the following formula

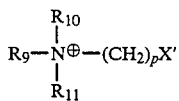

in which $R_9$ represents an alkyl or alkenyl group having from 10 to 20 carbon atoms, $R_{10}$ and $R_{11}$ independently represent an alkyl group having from 1 to 4 carbon atoms, p is an integer of 1 to 3, and X' represents $-COO^\ominus$ or $-SO_3^\ominus$ group.

(3) Imidazoline-type amphoteric surface active agents represented by the following formula

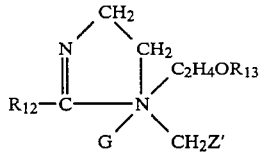

in which $R_{12}$ represents a fatty acid radical having from 10 to 20 carbon atoms on average, $R_{13}$ represents hydrogen, sodium or $CH_2COOMe$, and Z' represents COOMe, $CH_2COOMe$ or

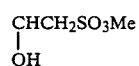

in which Me represents sodium, hydrogen or an organic base, and G represents OH, an acidic salt, or an anionic surface active sulfate or sulfide.

(4) Amidoamine compounds represented by the following general formula

in which $R_{14}$ represents a saturated or unsaturated aliphatic hydrocarbon group having from 7 to 21 carbon atoms, $R_{15}$ represents a hydrogen atom or a hydroxyalkyl group having from 1 to 4 carbon atoms, $R'_{15}$ may be the same as $R_{15}$ or is $-CH_2CH_2COOM$, and M' represents a hydrogen atom, an alkali metal, an ammonium salt, or an alkanolamine salt.

Of these shampoo bases, there are most preferably used anionic surface active agents such as linear or branched alkylsulfates having from 10 to 20 carbon atoms on average, polyoxyethylene alkylsulfates whose alkyl group has from 8 to 20 carbon atoms (the average number of addition moles ranging from 0.5 to 8), and olefin sulfonates having from 10 to 20 carbon atoms on average; and alkylamine oxides, alkylbetaines and imidazoline-type amphoteric surface active agents in which the alkyl group in each compound has from 10 to 20 carbon atoms on average. The shampoo bases may be used singly or in combination and are used in an amount of from 5 to 30%, preferably 10 to 25%, of the shampoo composition.

The shampoo composition according to the present invention should be in the form of paste or liquid using water in view of the manner of application thereof. The pH of the paste or liquid is preferred to range from 5.5 to 7.5.

Aside from the above-described essential ingredients, the shampoo composition of the invention may further comprise ingredients ordinarily used in known shampoo compositions, including a foam stabilizer such as alkylolamides; solubilizers such as propylene glycol, glycerine, urea and the like; viscosity modifiers such as ethanol, inorganic salts, higher alcohols, hydroxyethyl cellulose, hydroxypropyl cellulose and the like; pH controlling agents such as phosphoric acid, citric acid and the like; hair conditioners such as cationized cellulose, cationic surface active agents, glycerine ethylene glycol esters, carboxylic acid esters and the like; and perfumes, colorants, UV absorbers, antioxidants, anti-dandruff agents, bactericides, preservatives and the like.

The present invention is more particularly described by way of examples, which should not be construed as limiting the present invention.

EXAMPLES

Performances of shampoo compositions in examples were evaluated according to the following methods.

(1) Foaming Test Method (a) To an aqueous 1% solution of shampoo composition was added 0.5% of artificial soil, followed by agitating in a cylinder container at 40° C. for 5 minutes by means of a flat propeller under conditions where the propeller was rotated at a rotation frequency of 1000 r.p.m. and turned reversely at every 10 seconds. Thirty seconds after completion of the agitation, an amount of foams was measured for evaluation. The amount of foams is determined by foam height in cylinder container and is an indication of forming power.

(b) Organoleptic Evaluation Using Blanket

Twenty five grams of wool cloth was soaked with hot water (40° C.), on which was applied 0.5 g of a shampoo composition, followed by kneading for about 2 minutes. The amount of foams was organoleptically evaluated.

Evaluation Standard of Foaming

○ Good
◎ Moderate
△ Rather poor
× Poor

(2) Detergency Test Method (A) Artificially Soiled Cloth

An artificial oily soil was uniformly dispersed in solvent. #2003 cloth was brought to contact with the dispersion and dried to uniformly deposit the artificial oily soil thereon. The cloth was cut into 10 cm × 10 cm test pieces used for subsequent experiments.

(B) Washing Conditions and Method

In water of 4° DH was dissolved a shampoo composition to prepare one liter of a 3% shampoo aqueous solution. Five pieces of the artificially soiled cloth and the aqueous shampoo solution were placed, as they are, in a stainless beaker for targotmeter, followed by agitating at 100 r.p.m. at 40° C. for 10 minutes in the targotmeter. The pieces were each rinsed with running water, pressed with an iron and subjected to measurement of reflectivity.

(C) Calculation of Detergency Rate

The detergency rate was calculated according to the following equation.

The reflectivities of the original cloth prior to washing and before and after washing of soiled cloth at 460 mμ were measured by the use of an autographic recording colorimeter, from which the detergency rate (%) was calculated according to the following equation.

$$\text{Detergency rate (\%)} = \frac{\text{Reflectivity after washing} - \text{Reflectivity before washing}}{\text{Reflectivity of original cloth} - \text{Reflectivity before washing}} \times 100$$

The rate was indicated as an average of five cloths. The pH of the aqueous shampoo solution prior to washing was found to be 5.5.

(D) Extraction of Residual Lipid

The soiled cloth after the washing was subjected to extraction for 4 hours by the Soxlet extraction method using an extraction solvent of chloroform/methanol (50% v/v). Thereafter, the extract was dried under reduced pressure using a rotary evaporator.

(E) Calculation of Residue of Triglyceride

To the extract obtained by drying in (D) was added a given amount of chloroform for dissolution, after which a predetermined amount of the solution was spottily applied onto a silica gel plate (20 cm × 20 cm, using Wako gel B5) for thin-layer chromatography, made by ourselves, followed by developing with a first developer solution of benzene/hexane (50/50% v/v) to about 18 cm of the plate. Subsequently, it was developed with a second developer solution of hexane/diethyl ether/acetic acid (70/30/1 % v/v) to about 12 cm of the plate, followed by spraying 50% v/v sulfuric acid as usual and heating for color development. Thereafter, residual triglyceride was quantitatively determined using a densitometer (made by Shimadzu Seisakusho), from which the residual rate was calculated.

EXAMPLE 1

Shampoo compositions of the following formulations were prepared to evaluate their performances by the foaming and detergency tests. The results are shown in Table 1.

TABLE 1

| Composition/ Evaluation | Comparative Product 1 | Comparative Product 2 | Comparative Product 3 | Product 1 of Invention |
|---|---|---|---|---|
| Sodium Polyoxyethylene (2.5) Lauryl Ether Sulfate | 10 | 10 | 10 | 10 |
| Polyoxyethylene (80) Hardened Castor Oil | — | 5 | — | 5 |
| Polyoxyethylene (4) Adduct of Lauric alkanolamide | — | — | 5 | — |
| Sodium N—lauroyl-N—methyl-beta-alanine | — | — | 5 | 5 |
| Phosphoric Acid | suitable amount | suitable amount | suitable amount | suitable amount |
| pH (5% Aqueous Solution) | 5.5 | 5.5 | 5.5 | 5.5 |
| Foaming Power (mm) Artificial Soil Added | 109 | 32 | 65 | 98 |
| Foaming Power Organoleptic Evaluation Using Wool Cloth | ○ | × | △ | ○ |

TABLE 1-continued

| Composition/ Evaluation | Comparative Product 1 | Comparative Product 2 | Comparative Product 3 | Product 1 of Invention |
|---|---|---|---|---|
| Detergency Rate (%) | 48.8 | 44.3 | 47.5 | 51.3 |
| Residue of Triglyceride (%) | 10.3 | 7.9 | 9.4 | 7.0 |

EXAMPLE 2

Shampoo compositions of the following formulations were prepared to evaluate the foaming strength and detergency rate. The results are shown in Table 2.

TABLE 2

| Composition/ Evaluatoin | Comparative Product 4 | Comparative Product 5 | Comparative Product 6 | Comparative Product 7 | Comparative Product 8 | Product 2 of Invention |
|---|---|---|---|---|---|---|
| Sodium Polyoxyethylene (2.5) Lauryl Ether Sulfate | 12 | 12 | 12 | 12 | 12 | 12 |
| Diethanolamine Laurate | 3 | 3 | 3 | 3 | 3 | 3 |
| Polyoxyethylene (3) Alkyl(*) Ether | — | — | 0.8 | 0.8 | 0.8 | 0.8 |
| Polyoxyethylene (120) Hardened Castor oil | — | 0.8 | 0.8 | 0.8 | 0.8 | 0.8 |
| Sodium N—lauroyl-N—methyl-beta-alanine | — | — | — | — | — | 3 |
| Sodium N—lauroylsarcosine | — | — | — | 3 | — | — |
| Sodium N—lauroylglutamate | — | — | — | — | 3 | — |
| Phosphoric Acid | suitable amount | suitable amount | suitable amount | suitable amount | suitable amount | suitable amout |
| pH | 5.5 | 5.5 | 5.5 | 5.5 | 5.5 | 5.5 |
| Foaming Power (mm) No Artificial Soil Added | 230 | 220 | 210 | 220 | 220 | 230 |
| Foaming Power (mm) Artificial Soil Added | 120 | 101 | 72 | 103 | 92 | 119 |
| Foaming Power Organoleptic Evaluation Using Wool Cloth | ⊚-○ | △ | × | △ | △ | ⊚-○ |
| Detergency Rate (%) | 48.3 | 49.2 | 50.0 | 51.0 | 50.4 | 54.0 |
| Residue of Triglyceride (%) | 10.9 | 7.1 | 6.7 | 6.0 | 6.9 | 3.9 |

(Note) (*)Linear and branched alkyl group having from 11 to 15 carbon atoms.

EXAMPLE 3

Shampoo compositions of the following formulations were prepared for evaluation by the foaming test. The results are shown in Table 3.

TABLE 3

| Composition/ Evaluation | A | B | C | D | E | F | G |
|---|---|---|---|---|---|---|---|
| Sodium Polyoxyethylene (2.5) Lauryl Ether Sulfate | 15 | 15 | 15 | 15 | 15 | 15 | 15 |
| Lauric Diethanolamide | 2.5 | 2.5 | 2.5 | 2.5 | 2.5 | 2.5 | 2.5 |
| Polyoxyethylene (3) Alkyl(*) Ether | 0.8 | 0.8 | 0.8 | 0.8 | 0.8 | 0.8 | 0.8 |
| Polyoxyethylene (60) Hardened Castor Oil | 0.8 | 0.8 | 0.8 | 0.8 | 0.8 | 0.8 | 0.8 |
| Sodium N—lauroyl-N—methyl-beta-alanine | 1.5 | 1.5 | 1.5 | 1.5 | 1.5 | 1.5 | 1.5 |
| Phosphoric acid | suitable amount | suitable amount | suitable amount | suitable amount | suitable amount | suitable amount | suitable amount |
| pH | 5.0 | 5.5 | 6.0 | 6.5 | 7.0 | 7.5 | 8.0 |
| Foaming Power (mm) | 98 | 134 | 138 | 130 | 124 | 124 | 120 |

TABLE 3-continued

| Composition/Evaluation | A | B | C | D | E | F | G |
|---|---|---|---|---|---|---|---|
| Artifical Soil Added Foaming Power Organoleptic Evaluation Using | Δ | ◎ | ◎ | ◎ | ◎~○ | ◎~○ | ○ |

(Note) *Same as in Table 2.

What is claimed is:

1. In a shampoo composition of the type which comprises 5-30 wt % of an agent selected from the group consisting of an anionic surface active agent, an amphoteric surface active agent and a mixture thereof as a base, the improvement comprising adding:

(A) 0.5 to 10 wt % of an N-acyl-N-methyl-beta-alanine or its alt represented by the formula (I)

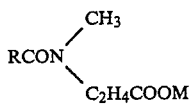

in which
R represents a linear or branched, saturated or unsaturated hydrocarbon group having from 7 to 21 carbon atoms, and
M represents hydrogen, an alkali metal, ammonium, alkyl-substituted ammonium with an alkyl moiety having from 1 to 3 carbon atoms, alkanolamine having a hydroxyalkyl group having from 1 to 3 carbon atoms, and basic amino acid, and (B) 0.5 to 20 wt % of one or more of ethylene oxide-added type nonionic surface active agents selected from the group consisting of polyoxyethylene alkyl or alkenyl ethers, polyoxyethylene alkylphenyl ethers, polyoxyethylene fatty acid esters, and polyoxyethylene hardened castor oils.

2. The shampoo composition according to claim 1, wherein the ingredient (A) is N-lauroyl-N-methyl-beta-alanine or its sodium salt or triethanolamine salt.

3. The shampoo composition according to claim 1 or 2, wherein the composition has a pH ranging from 5.5 to 7.5.

4. The shampoo composition of claim 1, wherein (A) is selected from the group consisting of the compound of formula (I) wherein
RCO—is selected from the group consisting of lauroyl, myristoyl, palmitoyl, stearoyl, oleoyl, and isostearoyl;
M is alkali metals, ammonium, ($C_1$–$C_3$) alkyl-substituted ammonium, ($C_1$–$C_3$) alkanolamines or a basic amino acids selected from the group consisting of lysine and arginine.

5. The shampoo composition of claim 4 wherein the N-acyl-N-methyl-beta-alanine is in the form of a sodium or triethanolamine salt.

6. The shampoo composition of claim 1 wherein (A) is present in an amount of between 1 and 6%.

7. The shampoo composition of claim 1 wherein (B) is selected from the group consisting of
polyoxyethylene alkyl or alkenyl ethers; said alkyl or alkenyl group containing an average of 8 to 20 carbon atoms and said ethylene oxide being added in an amount of 3-20 moles,
polyoxyethylene alkylphenyl ethers wherein the alkyl group contains an average of 8 to 12 carbon atoms and said ethylene oxide being in an amount of 3 to 20 moles,
polyoxyethylene fatty acid esters; wherein said alkyl or alkenyl group contains an average of 8 to 20 carbon atoms and said ethylene oxide being added in an amount of 8 to 100 moles of ethylene oxide, and
polyoxyethylene hardened castor oil; said polyoxyethylene oxide added in an amount of 3 to 200 moles.

8. The shampoo composition of claim 7, wherein (B) is selected from the group consisting of polyoxyethylene alkyl, alkenyl ethers and polyoxyethylene hardened castor oils.

9. The shampoo composition of claim 1, wherein (B) is present in an amount of between about 1 and 10%.